United States Patent [19]
Patel

[11] Patent Number: 5,779,475
[45] Date of Patent: Jul. 14, 1998

[54] TONGUE SCRAPER

[76] Inventor: Deepty U. Patel, 2906 Whittington Pl., Tampa, Fla. 33618

[21] Appl. No.: 798,942

[22] Filed: Feb. 11, 1997

[51] Int. Cl.$^6$ ................................................ A61C 3/00
[52] U.S. Cl. .................. 433/141; 433/142; 15/236.08; 601/137
[58] Field of Search ........................ 433/141, 142, 433/143, 216; 132/319, 200; 15/236.01, 236.07, 236.08; 601/137, 138, 139

[56] References Cited

U.S. PATENT DOCUMENTS

| | | | |
|---|---|---|---|
| 577,074 | 2/1897 | Seitz | 15/236.07 |
| 790,228 | 5/1905 | Rohrer | 15/236.08 |
| 1,519,689 | 12/1924 | Maxson | 15/236.08 |
| 1,586,031 | 5/1926 | Duncan | 601/137 |
| 2,677,843 | 5/1954 | Goodman | 433/143 |
| 4,780,923 | 11/1988 | Schultheiss | 433/147 |
| 4,795,344 | 1/1989 | Brewer, Jr. | 433/142 |
| 5,032,082 | 7/1991 | Herrera | 433/142 |

Primary Examiner—Nicholas D. Lucchesi

[57] ABSTRACT

A tongue scraper including a handle extent with a first free end and a second end. Further provided is an intermediate gripping extent with a first end integrally coupled in collinear relationship with the handle extent. Also included is a scraping extent having a closed-loop configuration with a hollow center. The scraping extent includes a first end integrally coupled with a second end of the intermediate gripping extent. A second end of the scraping extent has teeth formed therein for scraping teeth of a user. The teeth are defined by a plurality of triangular cut outs. Such cut outs form a plurality of triangular wells and a plurality of teeth members which together define the teeth. The teeth members include linear beveled side extents and an arcuate top surface. The teeth are formed along less than ¼ the entire periphery of scraping extent. The triangular wells associated with the teeth have a depth that is less than ⅓ the height of the scraping extent.

17 Claims, 2 Drawing Sheets

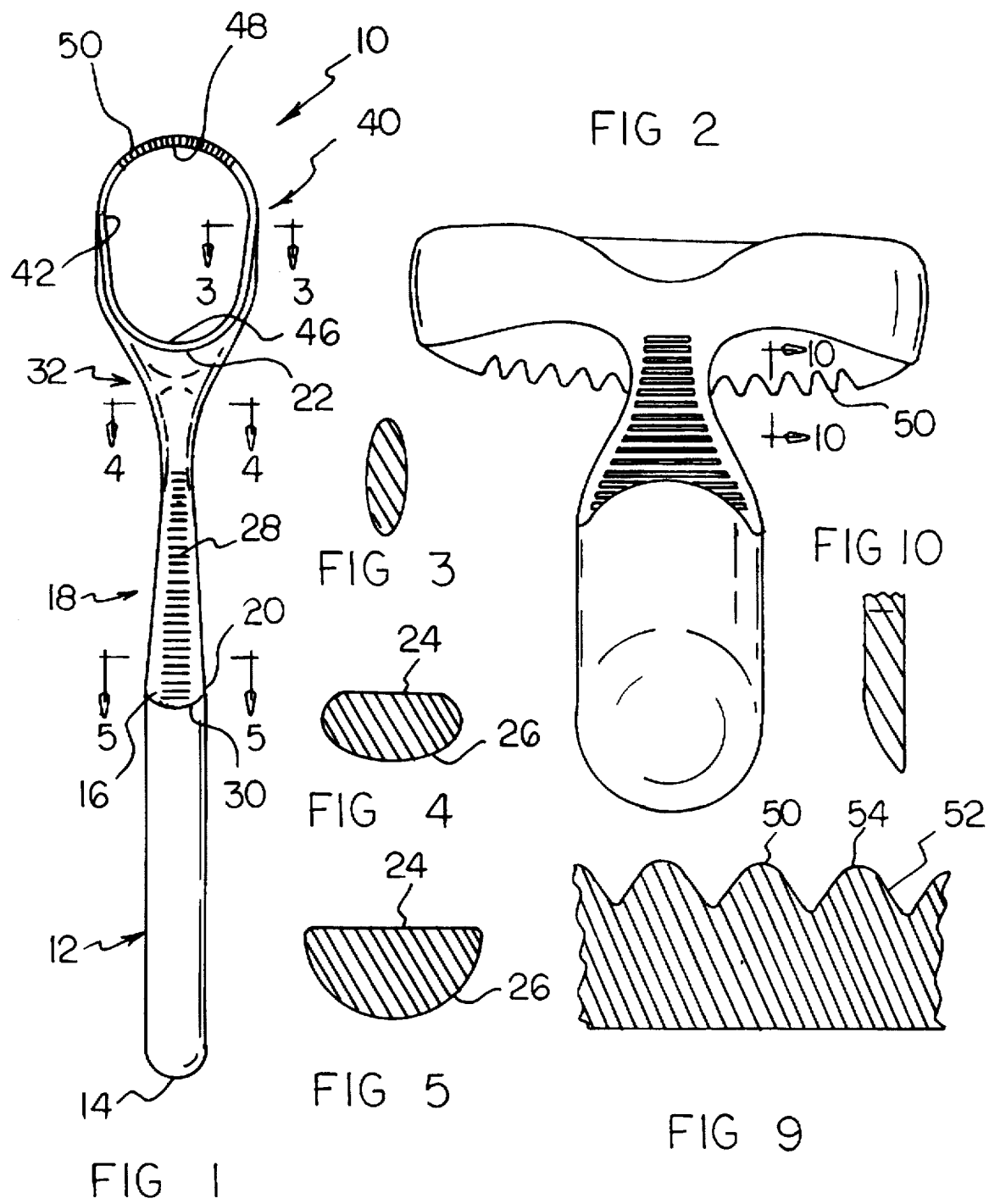

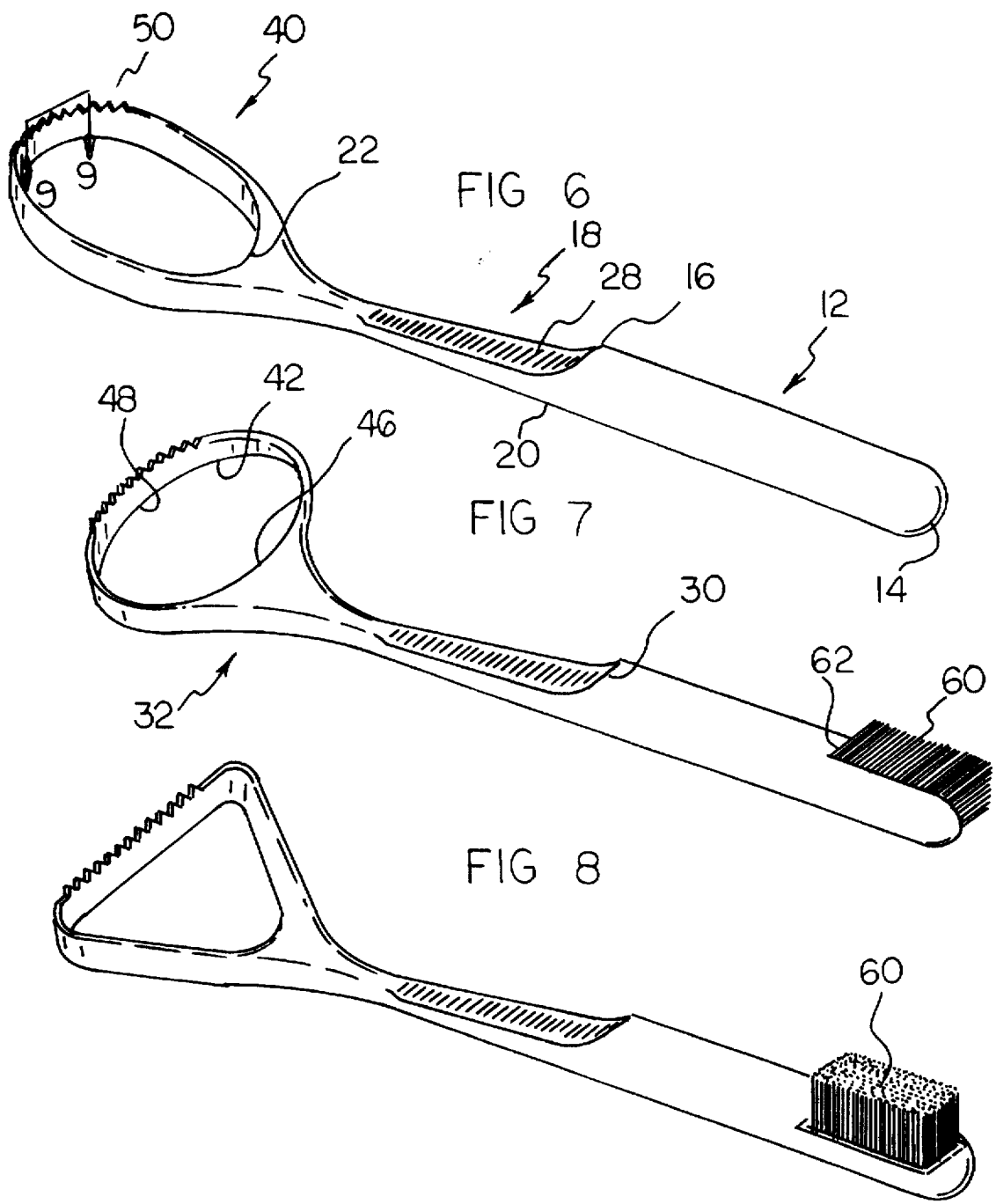

TONGUE SCRAPER

BACKGROUND OF THE INVENTION

1. Field of the Invention

The present invention relates to a tongue scraper and more particularly pertains to scraping a tongue with a conveniently utilized device that affords optimal results by means of uniquely configured teeth.

2. Description of the Prior Art

The use of tongue scrapers is known in the prior art. More specifically, tongue scrapers heretofore devised and utilized for the purpose of cleaning a tongue of a user are known to consist basically of familiar, expected and obvious structural configurations, notwithstanding the myriad of designs encompassed by the crowded prior art which have been developed for the fulfillment of countless objectives and requirements.

The prior art includes U.S. Pat. No. 5,217,475 which discloses a normally planar tongue scraper with a removable teethed element.

In this respect, the tongue scraper according to the present invention substantially departs from the conventional concepts and designs of the prior art, and in so doing provides an apparatus primarily developed for the purpose of scraping a tongue with a conveniently utilized device that affords optimal results by means of uniquely configured teeth.

Therefore, it can be appreciated that there exists a continuing need for a new and improved tongue scraper which can be used for scraping a tongue with a conveniently utilized device that affords optimal results by means of uniquely configured teeth. In this regard, the present invention substantially fulfills this need.

SUMMARY OF THE INVENTION

In view of the foregoing disadvantages inherent in the known types of tongue scrapers now present in the prior art, the present invention provides an improved tongue scraper. As such, the general purpose of the present invention, which will be described subsequently in greater detail, is to provide a new and improved tongue scraper which has all the advantages of the prior art and none of the disadvantages.

To attain this, the present invention essentially comprises a tongue scraper with a linear handle extent having a first free end and a second end. As shown in FIG. 2, the handle extent has a circular cross-sectional along an entire length thereof. The handle extent has a first predetermined length. Further provided is a linear intermediate gripping extent with a first end integrally coupled in collinear relationship with the second end of the handle extent. The intermediate gripping extent has a semi-circular cross-section with a top planar face and a bottom arcuate face, as shown in FIG. 5. For gripping purposes, the top face has a plurality of protrusions extending upwardly therefrom. The intermediate gripping extent has a second predetermined length less than the first predetermined length. Next provided is a scraping extent having a closed-loop configuration with a hollow center and an elliptical cross-section. Note FIG. 3. A line defined by foci of the elliptical cross-section resides perpendicular along its entire extent with a plane defined by the closed-loop configuration. Further, the plane defined by the closed-loop configuration forms a ten degree angle with a line defined by the handle extent and the intermediate gripping extent. The scraping extent includes a first end integrally coupled with the second end of the intermediate gripping extent. The scraping extent further has a second end. It should be noted that the scraping extent is a third predetermined length which is less than the second predetermined length. The second end of the scraping extent has a plurality of triangular notches formed therein defining teeth for scraping teeth of a user. As shown in great detail in FIG. 9, the teeth are defined by a plurality of triangular cut outs. The cut outs form a plurality of triangular wells and a plurality of teeth members. The teeth members each include linear beveled side extents and an arcuate top surface. The teeth are formed along less than ¼ the entire periphery of scraping extent. A depth of the triangular wells is less than ⅓ of the height of the scraping extent. Lastly, a brush is included with a plurality of bristles coupled to the first end of the handle extent and extending outwardly therefrom. Together, the bristles have a rectilinear configuration, wherein the length of the brush is less than ⅓ the first predetermined length.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved tongue scraper which has all the advantages of the prior art tongue scrapers and none of the disadvantages.

It is another object of the present invention to provide a new and improved tongue scraper which may be easily and efficiently manufactured and marketed.

It is a further object of the present invention to provide a new and improved tongue scraper which is of a durable and reliable construction.

An even further object of the present invention is to provide a new and improved tongue scraper which is susceptible of a low cost of manufacture with regard to both materials and labor, and which accordingly is then susceptible of low prices of sale to the consuming public, thereby making such tongue scraper economically available to the buying public.

Still yet another object of the present invention is to provide a new and improved tongue scraper which provides in the apparatuses and methods of the prior art some of the advantages thereof, while simultaneously overcoming some of the disadvantages normally associated therewith.

Still another object of the present invention is to scrape a tongue with a conveniently utilized device that affords optimal results by means of uniquely configured teeth.

Lastly, it is an object of the present invention to provide a new and improved tongue scraper including a handle extent with a first free end and a second end. Further provided is an intermediate gripping extent with a first end integrally coupled in collinear relationship with the handle extent. Also included is a scraping extent having a closed-loop configuration with a hollow center. The scraping extent includes a first end integrally coupled with a second end of the intermediate gripping extent. A second end of the scraping extent has teeth formed therein for scraping teeth of a user. The teeth are defined by a plurality of triangular cut outs. Such cut outs form a plurality of triangular wells and a plurality of teeth members. The teeth members include linear beveled side extents and an arcuate top surface. The teeth are formed along less than ¼ the entire periphery of scraping extent. The triangular wells associated with the teeth have a depth that is less than ⅓ the height of the scraping extent.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an illustration of the preferred embodiment of the tongue scraper constructed in accordance with the principles of the present invention.

FIG. 2 is a rear elevational view of the present invention.

FIG. 3 is a cross-sectional view of the present invention taken along lines 3—3 shown in FIG. 1.

FIG. 4 is a cross-sectional view of the present invention taken along lines 4—4 shown in FIG. 1.

FIG. 5 is a cross-sectional view of the present invention taken along lines 5—5 shown in FIG. 1.

FIG. 6 is a perspective view of a first embodiment of the present invention.

FIG. 7 is a perspective view of a second embodiment of the present invention.

FIG. 8 is a perspective view of a third embodiment of the present invention.

FIG. 9 is a close-up cross-sectional view of the teeth of the present invention taken along line 9—9 shown in FIG. 6.

FIG. 10 is a close-up cross-sectional view of the teeth of the present invention taken along line 10—10 shown in FIG. 2.

Similar reference characters refer to similar parts throughout the several views of the drawings.

DESCRIPTION OF THE PREFERRED EMBODIMENT

With reference now to the drawings, and in particular to FIG. 1 thereof, a new and improved tongue scraper embodying the principles and concepts of the present invention and generally designated by the reference numeral 10 will be described.

The present invention, the new and improved tongue scraper, is comprised of a plurality of components. Such components in their broadest context includes a handle extent, an intermediate gripping extent, a scraping extent, and a brush. Such components are individually configured and correlated with respect to each other so as to attain the desired objective.

More specifically, it will be noted that the system 10 of the present invention is a tongue scraper with a linear handle extent 12 having a first free end 14 and a second end 16. As shown in FIG. 2, the handle extent has a circular cross-sectional along an entire length thereof. The handle extent has a first predetermined length.

Further provided is a linear intermediate gripping extent 18 with a first end 20 integrally coupled in collinear relationship with the second end 22 of the handle extent. The intermediate gripping extent has a semi-circular cross-section with a top planar face 24 and a bottom arcuate face 26, as shown in FIG. 5. For gripping purposes, the top face has a plurality of protrusions 28 extending upwardly therefrom. As shown in FIG. 1, such protrusions take the form of linear bumps each with an axis that resides in perpendicular relationship with an axis defined by the intermediate extent and the handle extent. As shown in FIG. 2, such linear bumps are also formed in the bottom face of the intermediate gripping extent. It should be noted that at the interconnection 30 between the handle extent and the intermediate gripping extent, the top face of the intermediate extent curves upwardly to meet a top surface of the handle extent. As can be seen in FIG. 1, the intermediate extent tapers inwardly with a decreasing diameter from the first end to the second end thereof. Such holds true along the entire length of the intermediate gripping extent with the exception of a small portion 32 adjacent the second of the intermediate gripping extent whereat the intermediate gripping extent bevels outwardly doubling the width thereof. The intermediate gripping extent has a second predetermined length less than the first predetermined length.

Next provided is a scraping extent 40 having a closed-loop configuration with a hollow center 42 and an elliptical cross-section. Note FIG. 3. A line defined by foci of any portion of the elliptical cross-section resides perpendicular with a plane defined by the closed-loop configuration. Further, the plane defined by the closed-loop configuration forms a ten degree angle with a line defined by the handle extent and the intermediate gripping extent. The scraping extent further includes a first end 46 integrally coupled with the second end of the intermediate gripping extent. The scraping extent further has a second end 48. It should be noted that the scraping extent is a third predetermined length that is less than the first and second predetermined length. The second end of the scraping extent has scraping means including a plurality of triangular notches formed therein defining teeth for scraping teeth 50 of a user. The teeth have a thickness that is equal to the thickness of the scraping extent, wherein such thickness is less than 5% the width of the closed-loop configuration defined by the scraping extent. As shown in great detail in FIG. 9, the teeth are defined by a plurality of triangular cut outs. The cut outs form a plurality of triangular wells and a plurality of teeth members. The teeth members each include linear beveled side extents 52 and an arcuate top surface 54. Such arcuate surface defines an arc of circle which has a diameter of about ½ of an inch. The arc is constrained by an angle of approximately 60 degrees. The teeth are formed along less than ¼ the entire periphery of scraping extent. A depth of the triangular wells is less than ⅓ of the height of the scraping extent. Such height is depicted in FIG. 9. As shown in FIG. 10, the teeth further have a rear vertical surface and a front beveled surface. It should be noted that the rear vertical surface corresponds to the inner periphery of the scraping extent. Such surface is also the leading edge when the present invention is employed for scraping a tongue of the user.

In the first embodiment shown in FIGS. 1 & 6, the closed loop configuration takes the form of an oval with a pair of wide curves and a pair of tight curves wherein the teeth are formed on one of the tight curves and another tight curve is integrally coupled to the intermediate gripping extent. As shown in FIG. 7, a second embodiment is depicted with the closed loop configuration also taking the form of an oval with a pair of wide curves and a pair of tight curves. In such embodiment, however, the teeth are formed on one of the wide curves and another wide curve is integrally coupled to the intermediate gripping extent. As can be seen in FIG. 7, the axis defined by the handle and intermediate extent is slightly offset from the center of the oval. Finally, in a third embodiment, the closed loop configuration takes the form of an equilateral triangle. As shown in FIG. 8, the teeth of the present embodiment are formed on a side thereof. Also, an apex of the triangle that resides opposite the teeth is integrally coupled to the intermediate gripping extent.

Lastly, a brush 60 is included with a plurality of bristles coupled to the first end of the handle extent and extending outwardly therefrom. Together, the bristles have a rectilinear configuration, wherein the length of the brush is less than ⅓ the first predetermined length. Further, as shown in FIG. 8, the brush resides in a recess 62 formed in the handle extent. Preferably, the bristles extend in a direction similar to the direction the scraping means extend, as shown in FIG. 8. In the alternative, the bristles extend in a side direction perpendicular to the direction the scraping means extend. Note FIG. 7. Still another option would be to exclude the brush as shown in FIG. 6.

The present invention thus provides a brush and tongue scraper that is convenient to use and affords optimal results.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A new and improved tongue scraper comprising, in combination:

a linear handle extent with a first free end and a second end, the handle extent having a circular cross-sectional along an entire length thereof with the handle extent being a first predetermined length;

a linear intermediate gripping extent with a first end integrally coupled in collinear relationship with the second end of the handle extent, the intermediate gripping extent having a semi-circular cross-section with a top planar face and a bottom arcuate face, the top face having a plurality of gripping protrusions extending upwardly therefrom, the length of the intermediate gripping extent being a second predetermined length less than the first predetermined length;

a scraping extent having a closed-loop configuration with a hollow center and an elliptical cross-section wherein a line defined by the foci of the elliptical cross-section resides perpendicular along its entire extent with a plane defined by the closed-loop configuration, the plane defined by the closed-loop configuration further forming a ten degree angle with a line defined by the handle extent and the intermediate gripping extent, the scraping extent including a first end integrally coupled with the second end of the intermediate gripping extent and a second end, the scraping extent being a third predetermined length less than the second predetermined length, the second end of the scraping extent having a plurality of triangular notches formed therein defining teeth for scraping a tongue of a user; and a brush including a plurality of bristles coupled to the first end of the handle extent and extending outwardly therefrom, the bristles together having a rectilinear configuration, wherein the length of the brush is less than ⅓ the first predetermined length;

said teeth defined by a plurality of triangular cut outs, the cut outs forming a plurality of triangular wells and a plurality of teeth members, the teeth members each including linear beveled side extents, an arcuate top surface, a rear vertical surface and a front beveled surface, wherein the teeth are formed along less than ¼ the entire periphery of scraping extent and a depth of the triangular wells is less than ⅓ the height of the scraping extent.

2. A tongue scraper comprising:

a handle extent with a first free end and a second end;

an intermediate gripping extent with a first end coupled with the second end of the handle extent; and a scraping extent including a first end integrally coupled with the second end of the intermediate gripping extent and a second end, the second end of the scraping extent having scraping means for scraping a tongue of a user;

said scraping means including teeth defined by a plurality of triangular cut outs, the cut outs forming a plurality of triangular wells and a plurality of teeth members;

wherein the intermediate gripping extent has a semi-circular cross-section with a top planar face and a bottom arcuate face, the top face having a plurality of gripping protrusions extending upwardly therefrom;

wherein the scraping extent defines an elliptical cross-section wherein a line defined by the foci of the elliptical cross-section resides perpendicular with a plane defined by a closed-loop configuration.

3. A tongue scraper as set forth in claim 2 wherein the teeth members each include linear beveled side extents and an arcuate top surface.

4. A tongue scraper as set forth in claim 2 wherein a depth of the triangular wells is less than ⅓ the height of the scraping extent.

5. A tongue scraper as set forth in claim 2 wherein the plane defined by the scraping extent forms a ten degree angle with a line defined by the handle extent and the intermediate gripping extent.

6. A tongue scraper as set forth in claim 2 and further comprising a brush including a plurality of bristles coupled to the first end of the handle extent and extending outwardly therefrom, the bristles together having a rectilinear configuration.

7. A tongue scraper as set forth in claim 6 wherein the bristles extend in a direction similar to the direction the scraping means extends.

8. A tongue scraper as set forth in claim 6 wherein the bristles extend in a direction perpendicular to the direction that the scraping means extends.

9. A tongue scraper as set forth in claim 2 wherein the handle extent has a circular cross-sectional along an entire length thereof with the handle extent being a first predetermined length.

10. A tongue scraper as set forth in claim 9 wherein a length of the intermediate gripping extent is a second predetermined length less than the first predetermined length.

11. A tongue scraper comprising:

a handle extent with a first free end and a second end;

an intermediate gripping extent with a first end coupled with the second end of the handle extent; and a scraping extent including a first end integrally coupled with the second end of the intermediate gripping extent and a second end, the second end of the scraping extent having scraping means for scraping a tongue of a user;

said scraping means including teeth defined by a plurality of cut outs, the cut outs forming a plurality of wells and a plurality of teeth members, the teeth members each including beveled side extents and an arcuate top surface;

wherein the teeth are formed along less than ¼ the entire periphery of scraping extent.

12. A tongue scraper as set forth in claim 11 wherein a depth of the wells is less than ⅓ the height of the scraping extent.

13. A tongue scraper comprising:

a handle extent with a first free end and a second end;

an intermediate gripping extent with a first end coupled with the second end of the handle extent; and a scraping extent including a first end integrally coupled with the second end of the intermediate gripping extent and a second end, the second end of the scraping extent having scraping means for scraping a tongue of a user;

said scraping means including teeth defined by a plurality of triangular cut outs, the cut outs forming a plurality of triangular wells and a plurality of teeth members;

wherein the scraping extent forms a closed loop configuration which has the shape of an oval with a pair of wide curves and a pair of tight curves wherein the scraping means is formed on a first one of the curves and a second one of the curves situated opposite the first one of the curves is integrally coupled to the intermediate gripping extent.

14. A tongue scraper as set forth in claim 13 wherein the first one of the curves and the second one of the curves include the wide curves.

15. A tongue scraper as set forth in claim 13 wherein the first one of the curves and the second one of the curves include the tight curves.

16. A tongue scraper comprising:

a handle extent with a first free end and a second end;

an intermediate gripping extent with a first end coupled with the second end of the handle extent; and a scraping extent including a first end integrally coupled with the second end of the intermediate gripping extent and a second end, the second end of the scraping extent having scraping means for scraping a tongue of a user;

said scraping means including teeth defined by a plurality of cut outs, the cut outs forming a plurality of wells and a plurality of teeth members, the teeth members each including a rear surface and a front bevelled surface;

wherein the scraping extent forms a closed loop configuration.

17. A tongue scraper as set forth in claim 16 wherein the scraping extent forms a closed loop configuration which has the shape of an equilateral triangle with the scraping means formed on a side thereof and an apex of the triangle residing opposite the teeth being integrally coupled to the intermediate gripping extent.

* * * * *